United States Patent [19]

Lehmann et al.

[11] Patent Number: 5,422,121
[45] Date of Patent: Jun. 6, 1995

[54] ORAL DOSAGE UNIT FORM

[75] Inventors: Klaus Lehmann, Rossdorf; Ottilie E. E. Kehr-Dreher, Griesheim; Giuseppe Di Pascale, Weiterstadt, all of Germany

[73] Assignee: Röhm GmbH, Darmstadt, Germany

[21] Appl. No.: 106,539

[22] Filed: Aug. 16, 1993

Related U.S. Application Data

[63] Continuation-in-part of Ser. No. 790,744, Nov. 8, 1991, abandoned.

[30] Foreign Application Priority Data

Nov. 14, 1990 [DE] Germany ............... 9015551 U

[51] Int. Cl.⁶ .................... A61K 9/24; A61K 9/28
[52] U.S. Cl. ............................... 424/464; 424/472; 424/474; 424/475; 424/479; 424/482; 424/487; 424/488; 424/493; 424/497
[58] Field of Search ............ 424/479, 482, 461, 462, 424/493, 497, 464

[56] References Cited

U.S. PATENT DOCUMENTS 4,968,508  11/1990  Oren et al. ............ 424/468
5,015,480  5/1991  Childers et al. ........ 424/486

OTHER PUBLICATIONS

Ullmanns Encyklopädie der technischen Chemie, 4th edn., vol. 19 (1980) p. 235.
Römpps Chemie Lexikon, 9th edn. (1991), p. 2633.
Ullmann's Encyclopedia of Industrial Chemistry, vol. A11 (1988), p. 503.

*Primary Examiner*—Thurman K. Page
*Assistant Examiner*—James M. Spear

[57] ABSTRACT

Coating agents comprising a liquid phase, a polysaccharide decomposable in the colon, such as locust bean gum or guar gum, and a film forming polymer preferably having hydrophilic groups, which agent, when used for the coating of oral dosage unit forms, give coatings of high mechanical strength which are first decomposed under the influence of glycosidic enzymes in the colon; oral dosage unit forms incorporating such agents.

10 Claims, 1 Drawing Sheet

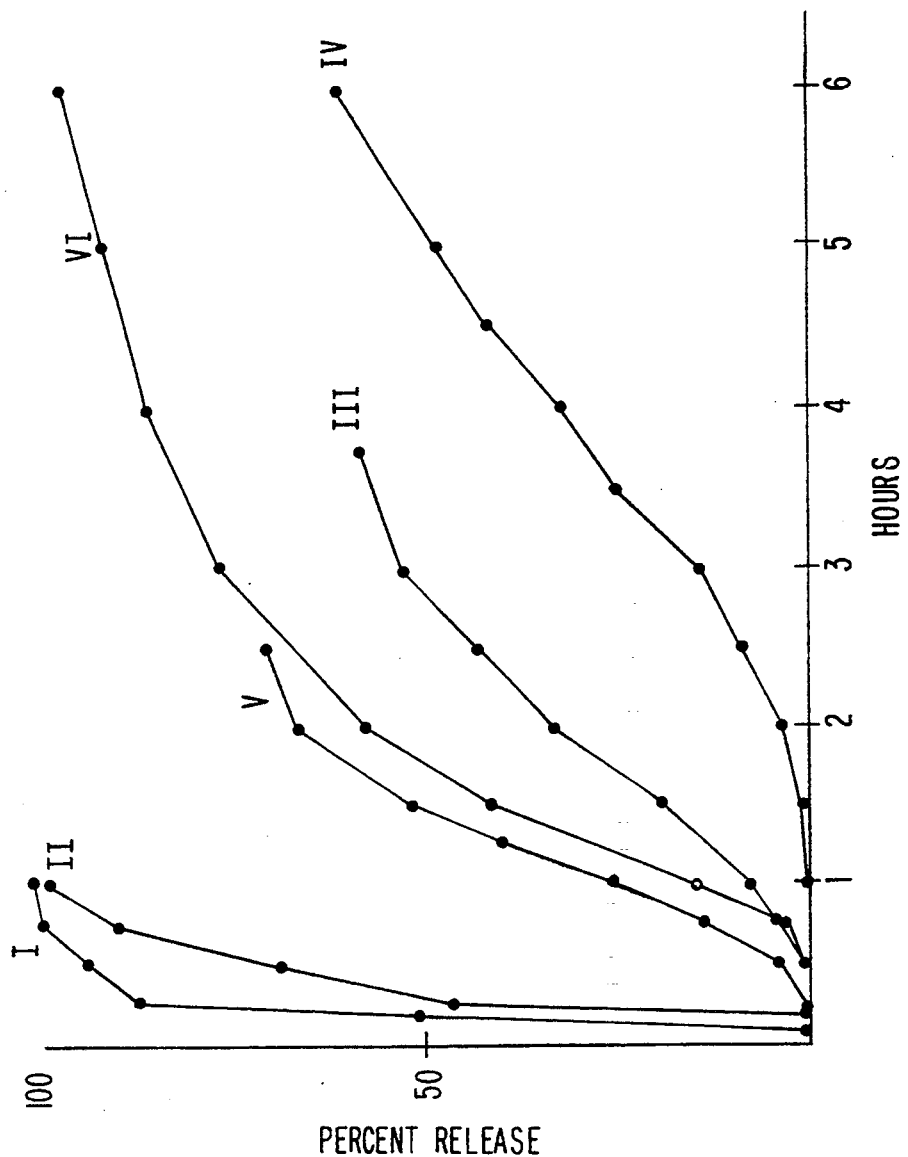

ORAL DOSAGE UNIT FORM

This application is a continuation-in-part of application Ser. No. 07/790,744 filed Nov. 8, 1991, now abandoned.

The present invention relates to an oral pharmaceutical dosage unit form containing at least one active ingredient and at least one shell material enclosing the active ingredient, as well as to a coating for pharmaceutical materials, which shell material and coating contain a liquid phase and a polysaccharide which decomposes in the colon.

STATE OF THE ART

It is generally known to provide oral pharmaceutical dosage unit forms with coatings which are resistant to stomach juice in order only to release the drug upon entry into the intestine. Numerous coating agents are known for this purpose, such as cellulose acetate phthalate (CAP), hydroxypropylmethyl cellulose phthalate (HPMCP), carboxymethyl ethyl cellulose (CMEC), polyvinylacetate phthalate (PVAP), and copolymers of methacrylic acid with acrylic acid esters and/or methacrylic acid esters (commercially available as "EUDRAGIT -L and -S" Röhm Pharma Gmbh).

It is taught in EP-B 152,038 how liberation of an active ingredient can be delayed further and further in the lower intestinal region by mixing a polymer which is water soluble at pH values from 5 to 8 with a water insoluble film forming polymer and increasing the amount of the latter in the mixture. In this, the dwell time of the drug in intestinal juice as well as the increasing pH value of the latter both play a role. A coating mixture is taught which will release the active material at a pH value of 7.5 only after more than three hours.

Control of the release of the active agent only according to the pH value expected in the colon usually involves considerable fluctuations of the release profile, depending on the constitution of the patient and his or her eating and living habits. The active agent may be released earlier or later than necessary, or even be lost unutilized with the feces. The desired release of active agent in the colon presents difficulties for these reasons. It has been sought to make use of environmental factors other than the dwell time in the intestinal tract and the pH value in order to effect a directed release of the active agent in the colon.

According to C. M. Lancaster and M. A. Wheatley, Polym. Prepr. (American Chemical Society, Division of Polymer Chemistry) 1989, 30(1), pages 480–481,the colon is differentiated from higher sections of the intestine by a heavier bacterial flora. Many of the bacteria present there produce glycosidic enzymes such as $\beta$-glucouronidase, $\beta$-xylosidase, $\alpha$- or $\beta$-glucosidase, $\beta$-galactosidase, mannanase, and galactomannanase, by which the designated natural polysaccharides are decomposed. The authors thus sought to coat oral drug dosage unit forms with a polysaccharide which was decomposable in the colon but which remained undissolved in the upper intestinal regions, so that dissolving of the coating and release of the active agent first occurred in the colon. However, it proved that the coated dosage unit forms dissolved rapidly already in the upper regions of the intestine. This was attributed to the insufficient film forming ability of the polysaccharides used and to the insufficient mechanical resistance which followed as a result. Attempts to make the coating more elastic and resistant with plasticizers remained unsuccessful. Triacetin, citric acid esters, polyethylene glycol, and glycerin did not have the effect hoped for. Thus, a further need for suitable plasticizing agents or for methods for ionic or chemical crosslinking of the polysaccharide was established.

K. H. Bauer (Deutsche Apotheker-Zeitung, 130. Jg., page 1172 of May 17, 1990) has developed polyurethane-oligosaccharide block copolymers as coatings for oral dosage unit forms which are resistant to stomach juices and are not decomposed in the small intestine. The glycolytic activity of the flora of the large intestine first cleaves the coating. It is possible in this way to transport medicaments, such as peptides, which are destroyed in the stomach or small intestine, to the large intestine without decomposition. A toxicological evaluation of these coatings has not yet been concluded.

PROBLEM AND SOLUTION

The invention has as its goal to prepare an oral dosage unit form or a film forming coating for oral dosage unit forms comprising polysaccharides which are decomposable in the colon, which are first decomposed under the influence of glycosidic enzymes, which provide a sufficient mechanical strength, and which are composed of toxicologically and pharmacologically unobjectionable components.

It was found that the task could be solved by an oral dosage unit form which contains at least one active ingredient and contains a polysaccharide decomposable in the colon in a shell material surrounding the active material if the shell material contains a film forming polymer material in admixture with the polysaccharide. The objects of the invention are, in addition to the dosage unit forms, coating agents for pharmaceuticals, such agents containing a liquid phase, a polysaccharide decomposable in the colon, and a film forming polymer. Surprisingly, the mixture also gives uniform, mechanically resistant coating films if the polysaccharide, which itself is not sufficiently film forming, makes up the predominant portion of the film. The shell material can, for example, surround, in the form of a coating, a core containing the active material. However, it can also form a matrix in which the active agent is distributed either homogeneously or in the form of crystals or as a granulate.

Polysaccharides decomposable in the colon and which are pharmacologically unobjectionable are available in sufficient number and quality for carrying out the invention. Likewise, numerous film forming polymer materials, resistant to stomach juice, are known and available commercially to serve as coating materials for oral dosage unit forms. The combination of these components is just as unobjectionable from the viewpoint of toxicology and pharmacology as are the components themselves. According to the invention, the combination leads to dosage unit forms which meet demands for mechanical strength and make possible the directed release of active ingredients in the colon.

Thus, the invention closes a gap in the palette of coating agents for dosage unit forms which had existed in the field of colon-soluble coatings and which had restricted the possibilities for galenic treatment.

The Shell Material

Polysaccharides decomposable in the colon are described in the publication of Lancaster and Wheatley cited earlier. For example, they are polysaccharides which are decomposable by glycosidic enzymes, particularly from the group of β-glucouronidase, β-xylosidase, α- or β-glucosidase, and β-galactosidase. Locust bean gum and guar gum are decomposed the best, which is why these polysaccharides are preferred. Xylan and tragacanth are somewhat more difficultly decomposable. In general, polysaccharides which contain considerable amounts, preferably about 20 to 100 percent by weight, of galactose and mannose units are most suitable.

Substances which have already proved themselves as coating agents for oral dosage unit forms are suitable as film forming polymeric materials. They are designated as film forming if their solutions or dispersions dry to form coherent, dry, non-tacky, shiny films. It is important that they combine a sufficient hardness with the necessary toughness, extensibility, and resistance to abrasion. Sometimes these properties can only be achieved by the addition of plasticizing agents such as triacetin, citric acid esters, polyethylene glycols, and glycerin.

Within the framework of the invention, the film forming polymer material meets the task of arranging the polysaccharide, which itself is not sufficiently film forming, into a galenically useful layer so that it can be attacked by glycosidic enzymes and assures the desired release of the active agent in the colon. This layer has the property of swelling in intestinal juice —also in the upper regions of the small intestine—without dissolving. Diffusion of the active ingredient through the swollen layer does not exceed 10 percent of the dose amount before the colon is reached, which for the most part is acceptable pharmacologically. If necessary, an undesired premature diffusion can be suppressed by an isolating layer of a galenic coating agent, resistant to stomach juice, between the core containing the active ingredient and the swellable layer. The swollen layer first decomposes and the enclosed active agent is first made accessible when glycosidic enzymes in the colon have an effect.

The release of active material in the stomach juice is fundamentally not desired. Thus, it is of advantage to use a film forming polymer material which is insoluble and not essentially swellable in stomach juice, but which is soluble, or at least swellable, in intestinal juice at pH values above 5. A film forming polymer material soluble in stomach juice can be used if the layer according to the invention is covered with a supplemental layer of a galenic coating agent resistant to stomach juice and soluble in intestinal juice. Swelling then sets in when the stomach is traversed and the supplemental coating is dissolved away by intestinal juice.

The swelling of the layer containing polysaccharide is enhanced if the film forming polymer material contains hydrophilic groups, e.g. carboxyl, carboxylate, tertiary amino, quaternary ammonium, or hydroxyl groups.

A preferred group of film forming polymers are the acrylic polymers. They preferably consist of 30 to 100 percent by weight of monomer units of lower alkyl esters of acrylic acid and/or of methacrylic acid, particularly those having 1 to 4 carbon atoms in the alkyl portion, and optionally up to 70 percent by weight of functional monomer units of ethylenically unsaturated, free radically copolymerizable monomers having a hydrophilic group. Acrylic polymers which consist exclusively of alkyl esters of acrylic acid and/or of methacrylic acid, or which contain at most small amounts, not exceeding 5 percent by weight of acrylic acid and/or of methacrylic acid, are soluble neither in stomach juice nor in intestinal juice. However, in the combinations according to the invention they give shells which are diffusion transparent or decompose in the colon.

With an increasing content of functional monomer, the solubility of the polymers in intestinal juice increases. So long as the functional groups are carboxyl or carboxylate groups, the speed of solution increase with increasing pH value. In the combinations with polysaccharide according to the invention, the resistance of the layer to digestive juices is on the whole greater than that of the acrylic polymers, despite a stronger swelling. Thus, such film forming polymers which, if used alone, would already dissolve in the upper regions of the intestine are also suitable for the shell material of the invention. Also film forming polymers having tertiary amino groups, which are insoluble in the intestine at a pH region above 5, but are permeable, can be used if they are protected during passage through the stomach by an over coating resistant to stomach juice.

The amount of the functional monomers having carboxyl or carboxylate groups in the acrylic polymers is preferably 30 to 50 percent by weight, that of monomers having tertiary amino or quaternary ammonium groups is preferably 5 to 10 percent by weight, based on the total weight of the polymer.

The functional monomer units of the acrylic polymers are preferably derived from acrylic acid and/or methacrylic acid or their derivatives. These include the salts of acrylic acid and/or of methacrylic acid, particularly the alkali metal or ammonium salts, as well as the esters or N-substituted amides thereof which have an hydroxyl group or a tertiary amino or quaternary ammonium group in the ester portion or in the N-substituents. Preferred hydroxyalkyl esters are 2-hydroxyethyl acrylate and methacrylate, 2-hydroxypropyl acrylate and methacrylate, and diethyleneglycol monoacrylate and monomethacrylate. Examples of monomers containing amino groups are:

2-dimethylamino-ethyl acrylate and methacrylate;
3-(N,N-dimethylamino)-propyl acrylate and methacrylate;
4-(N,N-dimethylamino)-butyl acrylate and methacrylate;
3-(N,N-dimethylamino)-propyl acrylamide and methacrylamide;
triethanolamine monoacrylate and monomethacrylate;
2-(dimethylaminoethyloxy)-ethyl acrylate and methacrylate;
2-imidazolyl-ethyl acrylate and methacrylate;
2-piperazinyl-ethyl acrylate and methacrylate;
2-piperazinyl-ethyl acrylamide and methacrylamide;
N,N-dimethylamino-neopentyl acrylate and methacrylate;
N,N-dimethylamino-neopentyl acrylamide and methacrylamide;
(1,2,2,6,6-pentamethyl-piperidyl-4) acrylate and methacrylate;
3-morpholino-propyl acrylamide and methacrylamide;
2-morpholino-ethyl acrylate and methacrylate;
2-(N,N-dibutylamino)-ethyl acrylate and methacrylate;
4-diethylamino-1-methyl-butyl acrylamide and methacryamide.

Monomers having quaternary ammonium groups are prepared therefrom by reaction with alkylating agents such as methyl chloride, ethyl bromide, inter alia.

The shell material can contain the polysaccharide and the film forming polymer material in a ratio by weight from 1:2 to 5:1, preferably from 1:1 to 4:1. Additionally, conventional additives such as fillers, dyes, pigments, plasticizers, film forming auxiliaries, preservatives, agents imparting luster, etc., may be present therein.

The Coating agent

The coating agent contains a liquid phase in addition to the polysaccharide and the film forming polymer. Because solvents, in which the two essential components of the invention commonly dissolve to form a clear solution have high viscosities even at low solids contents and the solutions are for this reason difficult to work with, in practice suspensions or dispersions of the components in the liquid phase are preferably used, providing that they dry to form a coherent film. As the liquid phase, for example, lower aliphatic alcohols, such as ethanol, propanol, butanol, and particularly isopropanol, are suitable, as are ketones such as acetone, or mixtures thereof with water. In this case, the preferred mixing ratio of alcohol or ketone to water, in parts by volume, is from about 2:1 to 1:2.

Suitably, the coating agent is prepared from an about 20 to 40 percent aqueous dispersion of the film forming polymer by diluting it with the same volume of alcohol and adding thereto a suspension of the polysaccharide in a water-alcohol mixture. Subsequently, further components can optionally be worked in. Aqueous dispersions of the film forming polymers are obtainable commercially or can be obtained from the powdered polymers by dispersing them in an aqueous phase, cf. EP-B 181,515, EP 88,951.

The liquid coating agent preferable has a solids content of 10 to 30 percent by weight, including all auxiliaries. It can be used according to conventional galenic methods for pelletizing or forming dragées or can be applied to dosage unit forms, e.g. by pouring or spraying in a coating kettle or by a fluidized bed method. The viscosity can be set to the desired value by dilution with solvents in admixture with water by appropriate choice of the amount of water. On evaporation of the liquid phase, film forming follows.

The Oral Dosage Unit Form

The oral dosage unit form can contain every active ingredient whose release in the colon is desired for pharmacological reasons. Among them are, for example, 5-aminosalicylic acid and bisacodyl. An important class of active agents which may first be released in the colon are those having a peptide or protein structure. They would be decomposed in the upper regions of the intestine by the body's own proteolytic enzymes. In the colon, the content of proteolytic enzymes is so far reduced that there is sufficient time for action or resorption. An active agent of this kind is, for example, insulin.

One can produce dosage, unit forms in which the active agent is dissolved in the liquid phase of the coating agent and the mass is dried. In this case, the active material is present in homogeneous distribution in a matrix formed by the shell material. For preparing matrix structures, the active ingredient, optionally together with further auxiliaries, can by granulated by moistening with the coating agent and then pressed. Predominantly, however, one starts with drug cores in the form of tablets, dragées, sachets, capsules, pellets, microspheres, granules, crystals, or powders and coats them so that the active agent and the shell material are present in separated phases.

According to a preferred embodiment of the invention, the core is first covered with a thin isolating layer of a film forming polymer material, resistant to stomach juice and soluble at pH 5 to 7 in intestinal juice, chosen so that it dissolves in the colon even under unfavorable conditions. Acrylic polymers having a relatively high amount of acrylic acid and/or methacrylic acid or of monomer units having quaternary ammonium groups are suitable. The layer of shell material according to the invention is applied thereover in a thickness of, for example, 10 to 150 microns. For tablet cores having a diameter of 6 to 10 millimeters, this corresponds as a rule to 1 to 15 percent of the solid weight. For smaller cores having a size of 0.1 to 2 millimeters, the amount of the shell material can be 5 to 40 percent by weight. Temporal delay of release of the active ingredient until under the effect of the glycosidic enzymes can be adapted by the layer thickness to the probable time of passage through the upper small intestine until reaching the colon. A fine adjustment of the layer thickness by tests in vivo is to be recommended. Preferably, this layer is covered with another coating, in one or more layers, which is resistant to stomach juice, but which dissolves on entry into the small intestine.

Larger dosage unit forms of this kind are used as such. Smaller coated particles can be filled into capsules or pressed into larger dosage units, whereby the shell material may optionally form a coherent matrix in which a majority of the original cores are distributed. If desired, such a unit may further be provided with a coating resistant to stomach juice.

After intake, the coating resistant to stomach juice remains unchanged on passage through the stomach. In the upper small intestine, the coating resistant to stomach juice dissolves. The now-exposed layer of the shell material according to the invention begins to swell and in this way can reach a layer thickness 5 to 10 times as great. By this swelling, an extensive attack on the isolating layer or—if no isolating layer is present—a premature dissolving out of the active ingredient can be delayed for 2 to 4 hours. By the inclusion of acid buffers, such as citric acid, phosphoric acid, acid phosphates, alginic acid, hyaluronic acid, carboxymethyl cellulose, polyacrylic acid, or methacrylic acid copolymers, a pH value below 5 can be maintained in the swollen layer for a long time, so that the digestive juice of the intestine is still not effective. In this way, the time for which the layer according to the invention is effective can be extended further.

The swollen layer of the shell material is first attacked in the colon at pH values of 6 to 7.5 by the glycosidic enzymes formed by the intestinal flora, so that it disintegrates mechanically and releases the core. This can now disintegrate quickly also and release the active agent in a short time.

A better understanding of the present invention and of its many advantages will be had from the following specific examples, given by way of illustration.

EXAMPLES

EXAMPLE 1

100 g of tablets containing methylene blue as a model active ingredient were first coated with a coating resistant to juice comprising a methacrylic acid—ethyl acrylate copolymer 50:50 percent by weight (commercial product "EUDRAGIT L 30 D" of Röhm Pharma GmbH). They were then prewarmed to 30° C. with warm air in a laboratory coating kettle rotating at 30 rpm and then coated with 14 ml of a liquid coating agent according to the invention in 0.2 to 0.3 ml portions. At the same time, drying proceeded at 50° C.

The coating agent was previously prepared in the following manner. 2.22 g of a 30 percent aqueous dispersion of a redispersed copolymer of methyl methacrylate, ethyl acrylate, and trimethyl ammonium-ethyl methacrylate chloride, 60:30:10 percent by weight (commercial product "EUDRAGIT RL 30 D" of Röhm Pharma GmbH) were mixed with 2 ml of isopropanol, whereby a viscous solution formed. A slurry of 2.22 g of guar gum in 10 ml of a mixture of equal portions by volume of isopropanol and water was added thereto and stirred to form a suspension.

After application of one third, two thirds, and the total amount of the coating agent, samples of the coated tablets were withdrawn and dried overnight at 40° C. The release of the methylene blue was investigated in a paddle apparatus according to the United States Pharmacopoeia at 75 rpm and 37° C., in each case with 800 ml of liquid, and determined colorimetrically. The results are reproduced in FIG. 1.

BRIEF DESCRIPTION OF THE DRAWINGS

Curves I to IV show the reduced release of active agent in synthetic intestinal juice at pH 6.8 in dependence on the thickness of the coating layer according to the invention. The time until release of 50 percent of the active agent is given in each case in parentheses.

Curve I: without any inventive shell material (10 min)
Curve II: 0.87 mg/cm$^2$ shell material (15 min)
Curve III: 1.70 mg/cm$^2$ shell material (2 hr, 40 min)
Curve IV: 2.60 mg/cm$^2$ shell material (5 hr). Curves V and VI show the release of active ingredient in synthetic intestinal juice at the same pH value and same temperature, but with the addition of 100 mg of glycosidase mixtures containing β-glucosidase, β-xylosidase, and galactomannanase.
Curve V: 1.70 mg/cm$^2$ shell material (1 hr, 20 min)
Curve VI: 2.60 mg/cm$^2$ shell material (1 hr, 40 min).
Curves I to IV demonstrate the release inhibiting effect of the coating of the invention in the absence of glycosidic enzymes, and Curves V and VI demonstrate the rapid release in the presence of glycosidic enzymes.

EXAMPLE 2

2.5 kg of tablets, 7.0 mm in diameter and having a unit weight of 140 mg, were agitated in a rotating coating kettle at 20 rpm, warmed to 30° C., and coated to be resistant to stomach juice by spraying with 370 g of "EUDRAGIT L 30 D" (30 percent aqueous dispersion of a copolymer of equal amounts of ethyl acrylate and methacrylic acid) together with 27.0 g of talc and 10.7 g of polywax in 165 g of water. Samples of the tablets showed no disintegration in synthetic stomach juice after 2 hours. The tablets were now coated in the same coating kettle at 40 rpm with a layer according to the invention of "EUDRAGIT L 30 D" and guar gum in a weight ratio of the dry substances of about 1:3. For this, 300 G of "EUDRAGIT L 30 D" were dissolved in 300 g of isopropanol and mixed with a slurry of 250 g of guar gum and 50 g of talc in a mixture of 800 g each of isopropanol and water and continuously sprayed on the tablets with a spray gun over a period of 155 minutes while at the same time drying at a core temperature of 30° C. with warm air. The tablets, post-dried for 2 hours at 40° C. in a circulating air drying cabinet show delayed release of active ingredient in a USP paddle apparatus in synthetic intestinal juice at pH 6.8. After 60 minutes, the tablets are swollen, but only 19 percent of the active material is liberated. On the addition of 100 mg of galactomannanase to the synthetic intestinal juice, over 80 percent of the active agent was already released after 45 minutes.

EXAMPLE 3

The test according to Example 2 was so modified that the tablets were not coated to be resistant to stomach juice, but were coated only with an inner isolating layer of 93 g of "EUDRAGIT L 30 D" (30 g dry weight) with 10 g of talc and 2.8 g of triethyl citrate as a plasticizer. These tablets disintegrate in stomach juice or water within 30 minutes. Subsequently, an intermediate layer of 280 g of "EUDRAGIT L 30 D", 232 g of guar gum, and 47 g of talc in isopropanol/water were applied in the same fashion. Over this yet, another outer layer, resistant to stomach juice comprising 480 g of "EUDRAGIT L 30 D" 54 g of talc, and 14.4 g of triethyl citrate was applied. These tablets do not disintegrate in a USP paddle apparatus in synthetic stomach juice within 2 hours and release only 1.7 percent of the active material, that is they are resistant to stomach juice. In synthetic intestinal juice at pH 6.8, the release of active ingredient is at first delayed (13.9 percent within 45 minutes), but is very rapid upon addition of galactomannanase (over 50 percent after 30 minutes).

EXAMPLE 4

Example 1 was repeated with 2.5 kg of tablets in a coating kettle having a 35 cm diameter under otherwise equal operating conditions. However, the swellable intermediate layer was formulated from 290 g of "EUDRAGIT RL 30 D" (30 percent aqueous dispersion of a copolymer of 30 parts of ethyl acrylate, 60 parts of methyl methacrylate, and 10 parts of trimethylammonium-ethyl methacrylate chloride), 320 g of guar gum, 70 g of talc, 780 g of isopropanol, and 780 g of water. The ratio by dry weight of "EUDRAGIT R 30 D" to guar gum here was about 1:4. In synthetic intestinal juice of pH 6.8, less than 1 percent of active agent was released from these tablets within 3.5 hours, and only 7 percent in 4 hours. In contrast, upon addition of 100 mg of galactomannanase per 900 ml of the same synthetic intestinal juice, 33 percent of the active agent was already in solution after 3 hours.

EXAMPLE 5

2.5 kg of tablets having a 7.0 mm diameter and 140 mg unit weight were coated directly, without any pre-isolation, with a mixture of 140 g of "EUDRAGIT S 100" (copolymer of 70 parts by weight of methyl methacrylate and 30 parts by weight of methacrylic acid), 346 g of guar gum, 74 g of talc, 1786 g of isopropanol, and 1312 g of water as a solution and dispersing agent. The tablets were added thereto in a rotating coating kettle of 35 cm diameter at 30–40 rpm with constant introduction of warm air at 50° C. in order to maintain the temperature of the cores at 30° C. At the end, the cores were dried for 2 hours at 40° C. in a circulating air drying cabinet. In a USP paddle apparatus with 900 ml of synthetic intestinal juice at pH 6.8, less than 2 percent of the active material was released after 30 minutes, whereas upon addition of 100 mg of galactomannanase, 55 percent was dissolved after 30 minutes and 90 percent after 60 minutes.

EXAMPLE 6

2 kg of prednisolone pellets having a content of active ingredient of 5 percent and a particle diameter of 0.8-1.2 mm were pre-isolated in a fluidized bed apparatus (Glatt GPCG1) by spray in a warm air stream at 30°-40° C. with 330 g of "EUDRAGIT L 30 D" (30 percent aqueous dispersion of a copolymer of equal parts of ethyl acrylate and methacrylic acid) with addition of 10 g of triethyl citrate as a plasticizer. Then 300 g of guar gum and 60 g of talc were suspended in a mixture of 1 kg each of isopropanol and water and mixed with a solution of 330 g of "EUDRAGIT RL 30 D" (30 percent aqueous dispersion of a copolymer of 30 parts of ethyl acrylate, 60 parts of methyl methacrylate, and 10 parts of trimethylammonium-ethyl methacrylate chloride in 330 g of isopropanol. The mixture was homogenized with a "ULTRA TURRAX" high speed homogenizer and sprayed in the same fluidized bed apparatus at 35°-45° C. inlet air temperature over a period of 125 minutes onto the pre-isolated cores. The coated pellets were dried over night at 40° C. on screens.

EXAMPLE 7

2.5 kg of theophylline powder having a grain size of 0.05-0.07 mm were agitated in a mixing vessel (Stephan mixer) at 200-500 rpm. 270 g of tragacanth were suspended in a mixture of 270 g of isopropanol and 270 g of water and mixed with a solution of 300 g of "EUDRAGIT RS 30 D" (30 percent aqueous dispersion of a copolymer of 30 parts ethyl acrylate, 65 parts methyl methacrylate, and 5 parts trimethylammonium-ethyl methacrylate chloride) in 300 g of isopropanol. This mixture was added in 100-200 ml portions to the theophylline powder with stirring and the moist mass passed through a sieve having a 1.0 mm mesh size. The granulate was dried for 24 hours at 40° C. and, after addition of 20 percent of cellulose powder ("AVICEL PH 102") and 0.5 percent of magnesium stearate, pressed into tablets.

EXAMPLE 8

Example 7 was modified in that guar gum, instead of tragacanth, was added in the same amount and granulated in the same way with 300 g of "EUDRAGIT RS 30 D" in 300 g of isopropanol. The dried granulate was also pressed into tablets upon addition of 20 percent of cellulose powder and 0.5 percent of magnesium stearate.

EXAMPLE 9

Example 7 was modified in that 270 g of dry guar gum were mixed into 2.5 kg of theophylline powder and then moistened only with the solution of "EUDRAGIT RL 30 D" in 300 g of isopropanol and dried. This at first very fine granulate was now again moistened with a mixture of 350 g of isopropanol and 350 g of water, pressed though a 1 mm sieve, and again dried as in Example 7.

What is claimed is:

1. An oral dosage unit form containing at least one active ingredient and having at least one shell material surrounding the active ingredient, the shell material comprising a polysaccharide, decomposable in the colon and containing 20 to 100 percent by weight of galactose and mannose units, and a film forming acrylic polymer in admixture therewith in a weight ratio of polysaccharide to film forming polymer of 1:1 to 4:1, the acrylic polymer comprising from 30 to 100 percent by weight of at least one monomer selected from the group consisting of lower alkyl esters of acrylic acid and lower alkyl esters of methacrylic acid and from 0 to 70 percent by weight of at least one further different monomer having a carboxyl group or a quaternary ammonium group, the further monomer being selected from the group consisting of acrylic acid, methacrylic acid, and compounds thereof.

2. An oral dosage unit form as in claim 1 wherein the polysaccharide is locust bean gum or guar gum.

3. A coating agent for oral medicaments, comprising a liquid phase; a polysaccharide, decomposable in the colon and containing 20 to 100 percent by weight of galactose and mannose units; and a film forming acrylic polymer in admixture with the polysaccharide in a weight ratio of polysaccharide to film forming polymer of 1:1 to 4:1, the acrylic polymer comprising from 30 to 100 percent by weight of at least one monomer selected from the group consisting of lower alkyl esters of acrylic acid and lower alkyl esters of methacrylic acid and from 0 to 70 percent by weight of at least one further different monomer having a carboxyl group or a quaternary ammonium group, the further monomer being selected from the group consisting of acrylic acid, methacrylic acid, and compounds thereof.

4. An oral dosage unit form as in claim 1 wherein the shell material is a coating which surrounds a core containing the active ingredient.

5. An oral dosage unit form as in claim 4 wherein the core has an isolating layer, soluble in intestinal juice, beneath the shell material.

6. An oral dosage unit form as in claim 1 wherein the shell material forms a matrix in which the active ingredient is distributed.

7. An oral dosage unit form as in claim 6 wherein the active ingredient is distributed homogeneously throughout the shell material matrix.

8. An oral dosage unit form as in claim 1 having a coating resistant to stomach juice but soluble in intestinal juice over the shell material.

9. A coating agent as in claim 3 wherein the film forming polymer is dispersed in the form of latex particles in the liquid phase.

10. A coating agent as in claim 9 wherein the liquid phase comprises at least one member selected from the group consisting of water and water miscible, lower aliphatic alcohols and ketones.

* * * * *